United States Patent
Ninomiya et al.

(10) Patent No.: US 6,420,575 B1
(45) Date of Patent: Jul. 16, 2002

(54) REFINING TREATMENT METHOD OF LIQUID REACTION MIXTURE OBTAINED FROM EPOXIDATION REACTION OF 1,5,9-CYCLODODECATRIENE

(75) Inventors: Kouhei Ninomiya; Tsunemi Sugimoto; Junichi Kugimoto; Mitsuo Yamanaka; Kohji Kaiso, all of Ube (JP)

(73) Assignee: Ube Industries Ltd., Ube (JP)

( * ) Notice: Subject to any disclaimer, the term of this patent is extended or adjusted under 35 U.S.C. 154(b) by 0 days.

(21) Appl. No.: 09/895,192

(22) Filed: Jul. 2, 2001

(30) Foreign Application Priority Data

Jul. 4, 2000 (JP) .......................... 2000-202688
May 18, 2001 (JP) .......................... 2001-149699

(51) Int. Cl.[7] .......................... C07D 301/12
(52) U.S. Cl. .......................... 549/531; 549/541
(58) Field of Search .................. 549/531, 541

(56) References Cited

U.S. PATENT DOCUMENTS

| | | | |
|---|---|---|---|
| 4,562,276 A | 12/1985 | Venturello et al. | 556/20 |
| 4,595,671 A | 6/1986 | Venturello et al. | 502/159 |
| 5,274,140 A | 12/1993 | Venturello et al. | 549/531 |

FOREIGN PATENT DOCUMENTS

| | | |
|---|---|---|
| EP | 0 033 763 A1 | 8/1981 |
| EP | 0 950 659 A2 A3 | 10/1999 |
| JP | 374235 B | 12/1985 |
| JP | 62 230778 A | 10/1987 |
| JP | 62234550 A | 10/1987 |
| JP | 05213919 A | 8/1993 |
| JP | 133471 B | 12/1993 |

OTHER PUBLICATIONS

Y. Ishii et al., "Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleavage of 1,2–Diols and Olefins", J. Org. Chem. vol. 53, 1988, pp. 3587–3593.

C. Venturello, "A New, Effective Catalytic System for Epoxidation of Olefins by Hydrogen Peroxide Under Phase–Transfer Conditions", J. Org. Chem. vol. 48, 1983, pp. 3831–3833.

L.I. Zakharkin et al., "Isomerization of Trans–1,2–Epoxy–Cis, Trans–5,9–Cyclododecadiene, Trans–1,2–Epoxy–Trans, Trans–5,9–Cyclododecadiene, and Trans–Epoxycyclododecane to the Corresponding Ketones by the Action of Lithium and Magnesium Iodides and Bromides", J. Org. Chem. of the USSR, vol. 26, No. 7, 1990, pp. 1291–1294.

*Primary Examiner*—Ba K. Trinh
(74) *Attorney, Agent, or Firm*—Morgan, Lewis & Bockius LLP

(57) ABSTRACT

After 1,5,9-cyclododecatriene is epoxidized with hydrogen peroxide in the presence of a catalyst containing a tungsten compound, a quaternary onium salt and a mineral acid, to obtain a liquid reaction mixture containing the resultant 1,2-epoxy-5,9-cyclododecadiene, the catalyst, non-reacted hydrogen peroxide and non-reacted 1,5,9-cyclododecatriene and being phase-separated into an oil phase fraction and an aqueous phase fraction, at least the oil phase fraction of the liquid reaction mixture is treated with an aqueous alkali solution to deactivate and remove the non-reacted hydrogen peroxide and the catalyst contained in at least the oil phase fraction.

19 Claims, No Drawings

REFINING TREATMENT METHOD OF LIQUID REACTION MIXTURE OBTAINED FROM EPOXIDATION REACTION OF 1,5,9-CYCLODODECATRIENE

BACKGROUND OF THE INVENTION (1) Field of the Invention

The present invention relates to a method of refining-treating a liquid reaction mixture obtained from an epoxidation reaction of 1,5,9-cyclododecatriene. More particularly, the method of the present invention relates to a method of refining-treating a liquid reaction mixture obtained from an epoxidation reaction of 1,5,9-cyclododecatriene with hydrogen peroxide in the presence of a catalyst. The refining-treatment method of the present invention is useful for the production of 1,2-epoxy-5,9-cyclododecadiene usable as an intermediate for laurolactam which is usable as a material for the production of nylon 12.

(2) Description of the Related Art

A method of epoxidizing an olefin compound with hydrogen peroxide is generally well known. For example, various methods of epoxidizing an olefin with hydrogen peroxide in the presence of a catalyst comprising, as examples, a tungsten compound, a quaternary onium salt and a mineral acid are disclosed in Japanese Examined Patent Publication No. 1-33,471 and No. 3-74235, and Japanese Unexamined Patent Publication No. 5-213,919, No. 62-230,778 and No. 62-234,550.

However, none of the above-mentioned publications discloses an industrial treating method for isolating an epoxy compound as a target product from a liquid reaction mixture obtained by an epoxidation reaction of the olefin compound with high safety and with high efficiency.

Usually, as a method of treating a liquid reaction mixture obtained from an epoxidation reaction of the olefin compound with hydrogen peroxide, a method in which an oil phase fraction and an aqueous phase fraction contained in the liquid reaction mixture are separated from each other by using a separator, and the separated oil phase fraction is subjected to distillation to collect the target epoxy compound, is utilized.

In the liquid reaction mixture obtained by an epoxidation reaction of 1,5,9-cyclododecatriene with hydrogen peroxide in the presence of a catalyst comprising a tungsten compound, a quaternary onium salt and a mineral acid, however, the oil phase fraction containing the resultant 1,2-epoxy-5,9-cyclododecadiene and the aqueous phase fraction exhibit a low liquid phase separation property from each other, and a portion of the aqueous phase fraction in several % is mixed with and suspended in the form of a plurality of liquid particles in the oil phase fraction. The portion of aqueous phase fraction suspended in the oil phase fraction is difficult to completely separate from the oil phase fraction, even after the oil phase fraction is left to stand for a long period.

The liquid particles, of the aqueous phase fraction mixed in the oil phase fraction, contain the tungsten compound and the mineral acid for the catalyst and the non-reacted hydrogen peroxide are dissolved therein. Therefore, when the oil phase fraction containing the aqueous phase fraction particles is subjected to distillation, the target product, namely 1,2-epoxy-5,9-cyclododecadiene is undesirably polymerized in the presence of the above-mentioned catalyst, and thus, a disadvantageous decrease in the yield of the target compound occurs.

Further, when the particles of the aqueous phase fraction mixed into the oil phase fraction contain a extremely strong acid compound, for example, phosphotungstic acid ($H_3PW_{12}O_{40}$), a phenomenon that the target 1,2-epoxy-5,9-cyclododecadiene vigorously reacts with the phosphotungstic acid ($H_3PW_{12}O_{40}$) to generate exothermic heat, may be created.

Also, a phenomenon that, in the distillation procedure, the non-reacted hydrogen peroxide and a by-product consisting of organic peroxide compounds which are dissolved in the aqueous phase fraction and the oil phase fraction, are respectively thermally decomposed, may be generated, and thus, the method in which the oil phase fraction of the liquid reaction mixture obtained from the epoxidation reaction of 1,5,9-cyclododecatriene is directly subjected to the distillation is not always safe in industrial practice.

Therefore, it is necessary to deactivate the non-reacted hydrogen peroxide and the residual catalyst compound contained in the oil phase fraction of the liquid reaction mixture and/or to remove them from the oil phase fraction by extraction, before the distillation of the oil phase fraction.

SUMMARY OF THE INVENTION

An object of the present invention is to provide a refining treatment method of a liquid reaction mixture obtained from an epoxidation reaction of 1,5,9-cyclododecatriene with hydrogen peroxide in the presence of a catalyst comprising a tungsten compound, a quaternary onium salt and a mineral acid, to obtain a liquid refined mixture from which the target 1,2-epoxy-5,9-cyclododecadiene can be collected, by distillation with an enhanced safety and with a high yield.

The above-mentioned object can be attained by the method of the present invention.

The refining treatment method of the present invention for a liquid reaction mixture obtained from an epoxidation reaction of 1,5,9-cyclododecatriene with hydrogen peroxide in the presence of a catalyst comprising a tungsten compound, a quaternary onium salt and a mineral acid, containing resultant 1,2-epoxy-5,9-cyclododecadiene, the catalyst, non-reacted hydrogen peroxide and non-reacted 1,5,9-cyclododecatriene, and being phase-separated into an oil phase fraction and an aqueous phase fraction, comprises refining-treating at least the oil phase fraction of the liquid reaction mixture with an aqueous alkali solution, to thereby deactivate and remove the non-reacted hydrogen peroxide and the catalyst contained in at least the oil phase fraction of the liquid reaction mixture.

In the refining treatment method of the present invention, for a liquid reaction mixture obtained from an epoxidation reaction of 1,5,9-cyclododecatriene, the aqueous alkali solution preferably has a pH value of 8 or more.

In the refining treatment method of the present invention, for a liquid reaction mixture obtained from an epoxidation reaction of 1,5,9-cyclododecatriene, in a system of the epoxidation reaction, the 1,5,9-cyclododecatriene contained in the reaction system serves as a reaction medium.

In the refining treatment method of the present invention, for a liquid reaction mixture obtained from an epoxidation reaction of 1,5,9-cyclododecatriene, the refining treatment of the liquid reaction mixture obtained from the epoxidation reaction with the aqueous alkali solution, is preferably controlled so that after the refining treatment, the aqueous phase fraction of the liquid reaction mixture exhibits a pH value of 7.0 or more.

In the refining treatment method of the present invention, for a liquid reaction mixture obtained from an epoxidation reaction of 1,5,9-cyclododecatriene, preferably the oil phase fraction is collected from the liquid reaction mixture obtained from the epoxidation reaction, and the collected oil phase fraction is subjected to the refining treatment with the aqueous alkali solution.

In the refining treatment method of the present invention, for a liquid reaction mixture obtained from an epoxidation reaction of 1,5,9-cyclododecatriene, and preferably after the refining treatment of the liquid reaction mixture obtained from the epoxidation reaction with the aqueous alkali solution is completed, the oil phase fraction is collected from the refining-treated liquid reaction mixture.

The method of the present invention for isolating 1,2-epoxy-5,9-cyclododecadiene comprises distilling the oil phase fraction collected and then refining-treated, or refining-treated and then collected, in accordance with the refining treatment method as mentioned above.

DESCRIPTION OF THE PREFERRED EMBODIMENTS

The refining treatment method of the present invention for the liquid reaction mixture obtained from the catalytic epoxidation reaction of 1,5,9-cyclododecatriene with.hydrogen peroxide will be explained in detail as follows.

The tungsten compounds usable for the epoxidation catalyst for the epoxidation reaction are preferably selected from inorganic acids containing tungsten atoms and salts thereof. The tungsten atom-containing acids and salts thereof include, for example, tungstic acid (wolframic acid) and salts thereof, for example, sodium tungstate, potassium tungstate, lithium tungstate, ammonium tungstate; and dodecatungstates, for example, sodium dodecatungstate, potassium dodecatungstate and ammonium dodecatungstate; and heteropoly-acids and salts thereof, for example, phosphotungstic acid, sodium phosphotungstate, silicotungstic acid, sodium silicotungstate, phosphovadadotungstic acid: and phosphomolybdotungstic acid, preferably tungstic acid, sodium tungstate, potassium tungstate, and phosphotungstic acid. There tungsten compounds may be employed alone or in a mixture of two or more thereof.

The tungsten compound for the epoxidation reaction of the method of the present invention is preferably employed in an amount of 0.0007 to 5% by weight, more preferably 0.002 to 3% by weight, in terms of tungsten atoms, based on the amount of 1,5,9-cyclododecatriene.

In the method of the present invention, the quaternary onium salts usable for the epoxidation catalyst include quaternary ammonium halides, for example, trioctylmethyl ammonium chloride, tridecylmethyl ammonium chloride, trioctylmethyl ammonium bromide, benzyldimethyltetradecyl ammonium chloride, benzyltriethyl ammonium chloride, dimethyldidodecyl ammonium chloride, benzyltributyl ammonium chloride, benzyltributyl ammonium iodide and phenyltrimethyl ammonium chloride; quaternary ammonium hydrogen sulfates; for example, trioctylmethyl ammonium hydrogen sulfate; quaternary ammonium perchlorates, for example, trioctylmethyl ammonium perchlorate; quaternary ammonium dihydrogen phosphates, for example, trioctylmethyl ammonium dihydrogen phosphate; quaternary ammonium nitrate, for example, trioctylmethyl ammonium nitrate; quaternary ammonium hydrosilicofluorate, for example, trioctylmethyl ammonium hydrosilicofluorate; and quaternary ammonium acetates, for example, trioctylmethyl ammonium acetate. Among the above-mentioned quaternary onium salts, preferably quaternary ammonium halides, more preferably trioctylmethyl ammonium chloride and tridecylmethyl ammonium chloride are employed.

The content of the quaternary onium salt in the epoxidation catalyst is preferably 0.0003 to 4% by weight, more preferably 0.003 to 2.5% by weight, based on the amount in weight of 1,5,9-cyclododecatriene.

The mineral acids usable for the epoxidation catalyst include, for example, phosphoric acids, sulfuric acids, hydrochloric acid, perchloric acid, hexafluorosilicic acid, nitric acid and tetrafluorosilicic acid. Preferably, phosphoric acid and sulfuric acid, more preferably phosphoric acid, are employed for the epoxidation catalyst. The above-mentioned mineral acids may be employed alone or in a mixture of two or more thereof.

The content of the mineral acid in the epoxidation catalyst is preferably 0.001 to 5% by weight, more preferably 0.005 to 3% by weight, based on the amount (by weight) of 1,5,9-cyclododecatriene.

There is no limitation to the concentration of hydrogen peroxide in the aqueous solution thereof usable for the epoxidation reaction for the method of the present invention. In consideration of safety in handling and economy of the epoxidation reaction, the aqueous hydrogen peroxide solution preferably has a concentration of hydrogen peroxide of 10 to 70% by weight. The aqueous hydrogen peroxide solution is preferably employed in a molar amount of hydrogen peroxide, of 0.05 to 1.2 times, more preferably 0.05 to 1.0 time, still more preferably 0.1 to 0.8 time the molar amount of 1,5,9-cyclododecatriene.

1,5,9-cyclododecatriene usable as a starting material for the epoxidation reaction may be a commercial grade, and the commercial grade 1,5,9-cyclododecatriene may be directly subjected to the epoxidation reaction without pre-treatment, or may be refined and then subjected to the epoxidation reaction. The 1,5,9-cyclododecatriene may be in any isomer form, for example, a cis-form or trans-form. The isomers may be mixed with each other.

In the epoxidation reaction in accordance with the method of the present invention, an organic solvent may be contained as a reaction medium in the reaction system. There is no limitation to the type of the organic solvent as long as the organic solvent cannot be evenly dissolved in water and does not obstruct the epoxidation reaction. The organic solvent for the reaction medium includes aliphatic halogenated hydrocarbons, for example, chloroform, dichloroethane, and dichloromethane; aliphatic non-halogenated hydrocarbons, for example, cyclohexane and n-heptane; and aromatic hydrocarbons, for example, benzene, toluene and xylene. The above-mentioned organic solvents may be employed alone or in a mixture of two or more thereof.

When the organic solvent is employed, the amount in weight of the organic solvent preferably does not exceeding 20 times,.and more preferably does not exceeding 10 times, the weight of 1,5,9-cyclododecatriene.

Preferably, the epoxidation reaction is carried out in a two liquid phase system consisting a liquid phase comprising 1,5,9-cyclododecadiene and an other liquid phase comprising the aqueous hydrogen peroxide solution, phase-separated from each other. For example, the epoxidation reaction is carried out by mixing 1,5,9-cyclododecatriene, an aqueous hydrogen peroxide solution and a catalyst comprising a tungsten compound, a quaternary onium salt and a mineral acid with each other in an atmosphere consisting of an inert gas, for example, nitrogen gas, and by heating the resultant mixture under the ambient atmospheric pressure or an increased pressure, while agitating the mixture. There is no limitation to the reaction temperature. Usually, the reaction temperature is preferably 20 to 120° C., more preferably 30 to 120° C.

In the refining treatment method of the present invention for the liquid reaction mixture obtained from the epoxidation reaction, an aqueous alkali solution may be directly added to the liquid reaction mixture. Otherwise, preferably, the liquid reaction mixture is subjected to a phase-separation procedure to separate an oil phase fraction from an aqueous phase fraction in the liquid reaction mixture, and then the oil phase fraction is subjected to the refining treatment procedure with the aqueous alkali solution. In the former, the resultant liquid mixture treated with the aqueous alkali solution is subjected to a phase-separation procedure to collect the treated oil phase fraction from the treated liquid mixture.

The aqueous alkali solution usable for the method of the present invention is an aqueous solution of at least one member selected from basic organic compounds of alkali metals and alkaline earth metals and ammonia. The aqueous alkali solution has a pH value of more than 7, preferably of 8 or more, more preferably 10 or more, still more preferably 11 or more. The basic organic compound includes hydroxides of alkali metals, carbonates of alkali metals, bicarbonates of alkali metals, sulfites of alkali metals, hydroxides of alkaline earth metals, carbonates of alkaline earth metals, bicarbonates of alkaline earth metals and sulfites of alkaline earth metals. Preferably the hydroxides of alkali metals, carbonates of alkali metals, bicarbonates of alkali metals and sulfites of alkali metals are employed and more preferably the hydroxides of alkali metals are employed.

Practical examples of the alkali metal hydroxides and alkaline earth metal hydroxides are potassium hydroxide, sodium hydroxide, magnesium hydroxide, barium hydroxide and calcium hydroxide.

Practical examples of the alkali metal carbonates and alkaline earth metal carbonates are potassium carbonate, sodium carbonate, magnesium carbonate and calcium carbonate.

Practical examples of the alkali metal bicarbonates are potassium bicarbonate and sodium bicarbonate.

Practical examples of the alkali metal sulfites are potassium sulfite and sodium sulfite.

Preferably, sodium hydroxide, potassium hydroxide and sodium sulfite, more preferably sodium hydroxide and potassium hydroxide are employed. The above-mentioned alkali metal compounds and alkaline earth metal compounds may be employed alone or in a mixture of two or more thereof.

The treatment procedure of the liquid reaction mixture with the aqueous alkali solution is not limited to a specific procedure. The treatment may be carried out by procedures in which at least the oil phase fraction of the liquid reaction mixture obtained from the epoxidation reaction is added with a solid alkali compound and then with water, or by procedures in which a solid alkali compound is dissolved in water to provide an aqueous alkali solution, and the aqueous alkali solution is mixed into the liquid reaction mixture obtained from the epoxidation reaction. In view of the ease of the procedures, preferably, an aqueous alkali solution is prepared and then the aqueous alkali solution is mixed into the liquid reaction mixture.

In the aqueous alkali solution, the concentration of the alkali compound is preferably 0.01 to 60% by weight, more preferably 0.1 to 30% by weight, still more preferably 0.5 to 10% by weight. The amount of the aqueous alkali solution to be added into the liquid reaction mixture is preferably controlled to an extent such that after the refining treatment is completed, the resultant treated liquid mixture has a pH value of 7 or more, more preferably 8.0 or more, still more preferably from 8 to 13.

Usually, the amount of the aqueous alkali solution used for the refining treatment for the liquid reaction mixture is preferably 1 to 20% by weight, more preferably 0.5 to 10% by weight, still more preferably 1.0 to 5% by weight, based on the total weight of the oil phase fraction in the liquid reaction mixture. If the alkali compound is employed in too large an amount, a new problem, that the aqueous phase fraction separated from the oil phase fraction must be specifically treated to remove the alkali, may occur.

In the refining treatment of the present invention, there is no limitation to the treatment temperature. Usually, the treatment temperature is preferably 0 to 120° C., more preferably 15 to 80° C., still more preferably 20 to 60° C. If the treatment temperature is too high, a trend that the yield of the target 1,2-epoxy-5,9-cyclododecadiene decreases may be observed.

The treatment apparatus usable for the refining treatment method of the; present Invention is not limited to specific types of apparatus, as long as the apparatus is provided with a stirring device enabling at least the oil phase fraction of the liquid reaction mixture obtained from the epoxidation reaction to be fully contacted with the aqueous alkali solution. For example, a vessel type reactor or a static type line mixer is preferably utilized for the refining treatment.

The refining treatment time for the method of the present invention is variable in response to the type of treatment apparatus. When the vessel type reactor is employed, the treatment time is preferably 1 to 90 minutes, more preferably 2 to 60 minutes, still more preferably 5 to 40 minutes. When the static mixer type reactor is employed, the treatment time is preferably 0.01 to 5 second, more preferably 0.05 to 3 seconds, still more preferably 0.1 to 2 seconds.

The refining treatment in accordance with the method of the present invention is usually carried out under the ambient atmospheric pressure, or optionally under increased pressure or reduced pressure.

The refining treatment of the liquid epoxidation reaction mixture in accordance with the method of the present invention can be carried out in a batch type reactor system or a continuous reactor system. In order to fully exhibit the effect of the present invention on an industrial scale, the method of the present invention is preferably carried out by using a continuous treating system comprising one or more treating apparatuses.

By applying the refining treatment in accordance with the method of the present invention, the deactivation and extraction of the residual catalyst contained in the liquid epoxidation reaction mixture and the decomposition of the non-reacted peroxide compounds remaining in the liquid epoxidation reaction mixture are promoted, and particularly, the residual catalyst is fully extracted and removed from the liquid reaction mixture.

Therefore, when the resultant alkali-treated liquid mixture is subjected to distillation, loss of the target compound, namely 1,2-epoxy-5,9-cyclododecadiene due to undesired polymerization and/or thermal decomposition of the target compound during the distillation is minimized and thus the target compound can be collected with high safety and with a high yield.

The target 1,2-epoxy-5,9-cyclododecadiene contained in the oil phase fraction of the liquid reaction mixture treated in accordance with the method of the present invention can be refined and collected by conventional distillation. The distilling apparatus usable for the alkali-treated liquid reaction mixture includes a conventional snider-type simple distilling apparatus, a regular packed column-type distilling apparatus, a perforated plate column-type distilling-apparatus and a bubble cap tower type distilling apparatus.

There is no limitation to the distillation conditions for the alkali-treated liquid reaction mixture. The distillation can be carried out under the ambient atmospheric pressure, a certain increased pressure or a reduced pressure. The distillation temperature is variable in response to the distillation pressure. Usually, the distillation temperature is preferably 200° C. or less more preferably 180° C. or less.

EXAMPLES

The present invention will be further illustrated by the following examples in comparison with the following comparative examples.

In the examples and comparative examples, the pH value of an aqueous alkali solution was determined by the following measurement.

An alkali compound in an amount of 1 mole was dissolved in 1 liter of ion-exchanged water, the pH value of the aqueous alkali solution was measured by a pH meter (model: D-24, made by HORIBA SEISAKUSHO) at room temperature.

Separately, the pH value of the ion-exchanged water was measured in the same manner as above.

Example 1

To prepare a typical liquid reaction mixture from an epoxidation reaction of 1,5,9-cyclododecatriene, 4500 g (27.8 moles) of 1,5,9-cyclododecatriene, 1.14 g (250 ppm) of trioctylmethyl ammonium chloride as an onium salt were placed in a glass flask with a capacity of 5000 ml, the resultant mixture was heated to a temperature of 75° C. while the flask was sealed with a nitrogen gas stream and the mixture was stirred.

After the temperature of the mixture reached 75° C., an aqueous solution of 393 g (6.9 moles) of a 60% by weight hydrogen peroxide, 1.14 g (250 ppm) of sodium tungstate and 1.14 g (250 ppm) of phosphoric acid was added dropwise to the 1,5,9-cyclododecatriene mixture over a time of 25 minutes. Then the resultant liquid reaction mixture was heated at a temperature of 75° C. for 90 minutes to complete the epoxidation reaction of 1,5,9-cyclododecatriene, and then cooled to room temperature.

A target typical liquid reaction mixture prepared by an epoxidation reaction of 1,5,9-cyclododecatriene was obtained in an amount of 4890 g.

The whole amount of the resultant liquid reaction mixture was placed in a separatory funnel with a capacity of 5,000 ml. The liquid reaction mixture was phase-separated into 4611 g of an oil phase fraction and 279 g of an aqueous phase fraction.

A glass flask having a capacity of 5,000 ml and equipped with a stirrer was charged with a portion of the oil phase fraction obtained by the phase-separation, in an amount of 750 g, and with 20 g of an aqueous solution containing 2.0% by weight of sodium hydroxide, and the resultant mixture in the glass flask was stirred at a temperature of 45° C. for 20 minutes.

Then the resultant alkali-treated mixture was cooled to room temperature and phase-separated by using a separatory funnel into an oil phase fraction and an aqueous phase fraction consisting of an aqueous solution containing sodium hydroxide. The separated aqueous phase fraction exhibited a pH value of 9.5.

The separated oil phase fraction was subjected to a plasma excitation emission spectroscopic analysis (ICP-AE S analysis) to determine the concentrations of catalytic elements, namely tungsten (W) and phosphorus (P). Also, the concentration of peroxide compounds in the oil phase fraction was determined by an Iodometry titration method. The analysis results are shown in Table 1.

As Table 1 shows, the alkali-treated, separated oil phase fraction had a W concentration of 10 ppm, a P concentration of 1 ppm or less and a peroxide concentration of 0.0056 millimole/g.

The alkali-treated, separated oil phase fraction in an amount of 500 g was distilled in a Sneader type distillator. In the distillation conditions, the distillation temperature for 1,5,9-cyclododecatriene was 76° C. under a pressure of 0.25 kPa, the distillation temperature for 1,2-epoxy-5,9-cyclododecadiene was 97° C. under a pressure of 0.25 kPa. As a distillation result, the target 1,2-epoxy-5,9-cyclododecladiene was collected in an amount of 163.1 g corresponding to a distillation yield of 99.4%.

Example 2

The same typical liquid reaction mixture obtained by the epoxidation reaction of 1,5,9-cyclododecatriene as in Example 1 was refining treated in the same manner as in Example 1, with the following exceptions.

An oil phase fraction, in an amount of 750 g, separated from the liquid reaction mixture and obtained from the epoxidation reaction, was placed, together with 75 g of an aqueous solution of 4.0% by weight of potassium hydroxide, in a glass flask having a capacity of 1000 ml and equipped with a stirrer. The mixture in the flask was stirred at a temperature of 25° C. for 10 minutes, and phase-separated into an oil phase fraction and an aqueous phase fraction.

The separated aqueous phase fraction and the separated oil phase fraction were separately subjected to the same analysis as in Example 1.

In the analysis results, the aqueous phase fraction had a pH value of 10.8, and the oil phase fraction had a W concentration of 8 ppm, a P concentration of 1 ppm or less, and a peroxide concentration of 0.0048 m mole/g.

The alkali-treated, separated oil phase fraction in an amount of 500 g was distilled in the same manner as in Example 1. As a result, 1,2-epoxy-5,9-cyclododecadiene was obtained in an amount of 163.5 g corresponding to a distillation yield of 99.7%.

The distillation yield is calculated in accordance with the following equation.

$$\text{Distillation yield (\%)} = \frac{[\text{Amount in gram of product collected by distillation}]}{[\text{Amount in gram of product contained in treated liquid reaction mixture subjected to distillation}]} \times 100$$

Example 3

The same typical liquid reaction mixture obtained by the epoxidation reaction of 1,5,9-cyclododecatriene as in Example 1 was refining treated in the same manner as in Example 2, with the following exceptions.

In the alkali treatment, the aqueous alkali solution contained 50 g of an aqueous solution of 10% by weight of sodium sulfite in place of the aqueous potassium hydroxide solution.

In the analysis results, the aqueous phase fraction had a pH value of 10.1, and the oil phase fraction had a W concentration of 15 ppm, a P concentration of 1 ppm or less, and a peroxide concentration of 0.0081 m mole/g.

The alkali-treated, separated oil phase fraction in an amount of 500 g was distilled in the same manner as in Example 1. As a result, 1,2-epoxy-5,9-cyclododecadiene was obtained in an amount of 162.5 g corresponding to a distillation yield of 99.2%.

Comparative Example 1

The same typical liquid reaction mixture obtained by the epoxidation reaction of 1,5,9-cyclododecatriene as in Example 1 was directly subjected to the same phase-separating procedure as in Example 1.

The separated oil phase fraction contained a portion of the aqueous phase fraction suspended therein and had a pH value of 3.6. The oil phase fraction was subjected to the same quantitative analysis for concentrations of W, P and peroxides as in Example 1.

In the analysis results, the oil phase fraction had a W concentration of 117 ppm, a P concentration of 4.1 ppm, and a peroxide concentration of 0.0163 m mole/g.

The non-alkali-treated, separated oil phase fraction in an amount of 500 g was directly distilled in the same manner as in Example 1. As a result, 1,2-epoxy-5,9-cyclododecadiene was obtained in an amount of 160.6 g corresponding to a distillation yield of 97.9%.

Comparative Example 2

The same typical liquid reaction mixture obtained by the epoxidation reaction of 1,5,9-cyclododecatriene as in Example 1 was refining treated in the same manner as in Example 2, except that the 4% by weight aqueous potassium hydroxide solution was replaced by a distilled water, and then phase-separated and analized in the same manner as in Example 2.

The separated aqueous phase fraction had a pH value of 6.2 and the separated oil phase fraction had a W concentration of 102 ppm, a P concentration of 3.6 ppm and a peroxide concentration of 0.0147 m mole/g.

The water-treated, separated oil phase fraction in an amount of 500 g was distilled under the same distillation conditions. The target 1,2-epoxy-5,9-cyclododecadiene was obtained in an amount of 161.2 g corresponding to a distillation yield of 98.2%.

In Table 1, the treatment conditions and results of Examples 1 to 3 and Comparative Examples 1 and 2 are shown.

TABLE 1

| | | Refining treatment with alkali | | | | | Analysis results of oil phase fraction | | | |
|---|---|---|---|---|---|---|---|---|---|---|
| | | Amount of oil phase fraction | Aqueous alkali solution | | Alkali treatment | | W | P | Peroxide | Distillation |
| Example No | Item | of liquid reaction mixture (ml) | Alkali concentration | Amount (g) | Temperature (° C.) | Time (min.) | concentration (ppm) | concentration (ppm) | concentration (m mole/g) | yield of ECD" (%) |
| Example | 1 | 750 | 2% NaOH | 20 | 45 | 20 | 10 | <1 | 0.0056 | 99.4 |
| | 2 | 750 | 4% KOH | 75 | 25 | 10 | 8 | <1 | 0.0048 | 99.7 |
| | 3 | 750 | 10% $Na_2SO_3$ | 50 | 25 | 10 | 15 | <1 | 0.0081 | 99.2 |
| Comparative Example | 1 | 750 | None | None | — | — | 117 | 4.1 | 0.0163 | 97.9 |
| | 2 | 750 | Distilled water | 75 | 25 | 10 | 102 | 3.6 | 0.0147 | 98.2 |

Note:
ECD" --- 1,2-epoxy-cyclododecadiene

Example 4

From a liquid reaction mixture obtained by an epoxidation reaction in a pilot plant scale, an oil phase fraction containing 22.0% by weight of 1,2-epoxy-cyclododecadiene, 80.2 ppm of tungsten (W), 8.2 ppm of phosphorus (P), 0.0179 m mole of peroxides and 76% by weight of non-reacted 1,5,9-cyclododecatriene which served as a reaction medium, was prepared.

The oil phase fraction in an amount of 200 g was mixed with 20 g of an aqueous solution of 1 mole/liter of sodium hydroxide (having a measured pH value of 13.6), and the resultant mixture was shaken at room temperature for 3 minutes, and then left to stand to allow it to phase-separate. The separated oil phase fraction was subjected to the same analysis as in Example 1. As a result, it was confirmed that the peroxide concentration of the oil phase fraction was reduced to 0.010 g m mole/g, the W concentration was reduced to 7.3 ppm and the P concentration was reduced to 1 ppm or less.

The analysis results are shown in Table 2.

Example 5

The same procedures as in Example 4 were carried out to refining treat the oil phase fraction, with the following exceptions.

The aqueous solution of 1 mole/liter of sodium hydroxide in an amount of 20 g (having a measured pH value of 13.6) was replaced by 20 g of an aqueous solution of 1 mole/liter of potassium hydroxide (having a measured pH value of 13.7).

The analysis results are shown in Table 2.

Example 6

The same procedures as in Example 4 were carried out to refining treat the oil phase fraction, with the following exceptions.

The aqueous solution of 1 mole/liter of sodium hydroxide in an amount of 20 g (having a measured pH value of 13.6) was replaced by 20 g of an aqueous solution of 1 mole/liter of sodium sulfite (having a measured pH value of 10.3).

The analysis results are shown in Table 2.

Example 7

The same procedures as in Example 4 were carried out to refining treat the oil phase fraction, with the following exceptions.

The aqueous solution of 1 mole/liter of sodium hydroxide in an amount of 20 g (having a measured pH value of 13.6) was replaced by 20 g of an ion-exchanged water (having a measured pH value of 6.7).

The analysis results are shown in Table 2.

The treatment conditions of Examples 4 to 7 and Comparative Examples 3 to 5 are shown, together with the analysis results, in Table 2.

TABLE 2

| | | Amount of oil phase fraction of liquid reaction mixture (ml) | Aqueous alkali solution | | | | Alkali treatment | | Analysis results of treated oil phase fraction | | |
|---|---|---|---|---|---|---|---|---|---|---|---|
| Example No | Item | | Type of alkali | Amount (g) | Concentration of alkali (mole/liter) | pH value | Temperature | Time (min.) | W concentration (ppm) | P concentration (ppm) | Peroxide concentration (m mole/g) |
| Oil phase fraction before refining treatment | — | — | — | — | — | — | — | — | 80.2 | 8.2 | 0.0179 |
| Example | 4 | 200 | NaOH | 20 | 1 | 13.6 | Room temp. | 3 | 7.3 | <1 | 0.0109 |
| | 5 | 200 | KOH | 20 | 1 | 13.7 | Room temp. | 3 | 9.2 | <1 | 0.0103 |
| | 6 | 200 | $Na_2SO_3$ | 20 | 1 | 10.3 | Room temp. | 3 | 15.2 | <1 | 0.0169 |
| | 7 | 200 | $NaHCO_3$ | 20 | 1 | 7.9 | Room temp. | 3 | 26.5 | 4.3 | 0.0151 |
| Comparative Example | 3 | 200 | $NaHSO_3$ | 20 | 1 | 3.8 | Room temp. | 3 | 63.2 | 4.1 | 0.0138 |
| | 4 | 200 | $Na_2S_2O_3$ | 20 | 1 | 6.7 | Room temp. | 3 | 14.2 | 3.7 | 0.0181 |
| | 5 | 200 | Distilled water | 20 | 1 | 6.7 | Room temp. | 3 | 81.2 | 8.2 | 0.0180 | was replaced by 20 g of an aqueous solution of 1 mole/liter of sodium hydrogen carbonate (having a measured pH value of 7.9).

The analysis results are shown in Table 2.

Comparative Example 3

The same procedures as in Example 4 were carried out to refining treat the oil phase fraction, with the following exceptions.

The aqueous solution of 1 mole/liter of sodium hydroxide in an amount of 20 g (having a measured pH value of 13.6) was replaced by 20 g of an aqueous solution of 1 mole/liter of sodium hydrogen sulfite (having a measured pH value of 3.8).

The analysis results are shown in Table 2.

Comparative Example 4

The same procedures as in Example 4 were carried out to refining treat the oil phase fraction, with the following exceptions.

The aqueous solution of 1 mole/liter of sodium hydroxide in an amount of 20 g (having a measured pH value of 13.6) was replaced by 20 g of an aqueous solution of 1 mole/liter of sodium thiosulfate (having a measured pH value of 6.7).

The analysis results are shown in Table 2.

Comparative Example 5

The same procedures as in Example 4 were carried out to refining treat the oil phase fraction, with the following exceptions.

When the refining treatment method, of the present invention, with an aqueous alkali solution is applied to at least an oil phase fraction of a liquid reaction mixture obtained from an epoxidation reaction of 1,5,9-cyclododecatriene with hydrogen peroxide in the presence of a catalyst comprising a tungsten compound, a quaternary onium salt and a mineral acid, containing the resultant 1,2-epoxy-5,9-cyclododecadiene, the catalyst, non-reacted hydrogen peroxide and non-reacted 1,5,9-cyclododecatriene, and being phase-separated into an oil phase fraction and an aqueous phase fraction, peroxide compounds and the catalyst contained in at least the oil phase fraction of the liquid reaction mixture are deactivated and removed and the target 1,2-epoxy-5,9-cyclododecadiene can be collected from the treated reaction mixture or oil phase fraction with high safety and with a high yield. Also, by the refining treatment method, the catalyst remaining in the liquid reaction mixture can be extract-treated with a high efficiency.

What is claimed is:

1. A refining treatment method of a liquid reaction mixture obtained from an epoxidation reaction of 1,5,9-cyclododecatriene with hydrogen peroxide in the presence of a catalyst comprising a tungsten compound, a quaternary onium salt and a mineral acid, containing resultant 1,2-epoxy-5,9-cyclododecadiene, the catalyst, non-reacted hydrogen peroxide and non-reacted 1,5,9-cyclododecatriene, and being phase-separated into an oil phase fraction and an aqueous phase fraction, which method comprises refining-treating at least the oil phase fraction of the liquid reaction mixture with an aqueous alkali solution, to thereby deactivate and remove the non-reacted hydrogen peroxide and the catalyst contained in at least-the oil phase fraction of the liquid reaction mixture.

2. The refining treatment method of a liquid reaction mixture obtained from an epoxidation reaction of 1,5,9-cyclododecatriene as claimed in claim 1, wherein the aqueous-alkali solution has a pH value of 8 or more.

3. The refining treatment method of a liquid reaction mixture obtained from an epoxidation reaction of 1,5,9-cyclododecatriene as claimed in claim 1, wherein, in a system of the epoxidation reaction, the 1,5,9-cyclododecatriene contained in the reaction system serves as a reaction medium.

4. The refining treatment method of a liquid reaction mixture obtained from an epoxidation reaction of 1,5,9-cyclododecatriene as claimed in claim 1, wherein the refining treatment of the liquid reaction mixture obtained from the epoxidation reaction, with the aqueous alkali solution, is controlled so that after the refining treatment, the aqueous phase fraction of the liquid reaction mixture exhibits a pH value of 7.0 or more.

5. The refining treatment method of a liquid reaction mixture obtained from an epoxidation reaction of 1,5,9-cyclododecatriene as claimed in claim 1, wherein the oil phase fraction is collected from the liquid reaction mixture obtained from the epoxidation reaction and the collected oil phase fraction is subjected to the refining treatment with the aqueous alkali solution.

6. The refining treatment method of a liquid reaction mixture obtained from an epoxidation reaction of 1,5,9-cyclododecatriene as claimed in claim 1, wherein, after the refining treatment of the liquid reaction mixture obtained from the epoxidation reaction with the aqueous alkali solution is completed, the oil phase fraction is collected from the refining-treated liquid reaction mixture.

7. A method of isolating 1,2-epoxy-5,9-cyclododecadiene comprising distilling the oil phase fraction collected and then refining-treated, or refining-treated and then collected, in accordance with the method as claimed in claim 5.

8. The refining treatment method of a liquid reaction mixture obtained from an epoxidation reaction of 1,5,9-cyclododecatriene as claimed in claim 2, wherein, in a system of the epoxidation reaction, the 1,5,9-cyclododecatriene contained in the reaction system serves as a reaction medium.

9. The refining treatment method of a liquid reaction mixture obtained from an epoxidation reaction of 1,5,9-cyclododecatriene as claimed in claim 2, wherein the refining treatment of the liquid reaction mixture obtained from the epoxidation reaction, with the aqueous alkali solution, is controlled so that after the refining treatment, the aqueous phase fraction of the liquid reaction mixture exhibits a pH value of 7.0 or more.

10. The refining treatment method of a liquid reaction mixture obtained from an epoxidation reaction of 1,5,9-cyclododecatriene as claimed in claim 3, wherein the refining treatment of the liquid reaction mixture obtained from the epoxidation reaction, with the aqueous alkali solution, is controlled so that after the refining treatment, the aqueous phase fraction of the liquid reaction mixture exhibits a pH value of 7.0 or more.

11. The refining treatment method of a liquid reaction mixture obtained from an epoxidation reaction of 1,5,9-cyclododecatriene as claimed in claim 2, wherein the oil phase fraction is collected from the liquid reaction mixture obtained from the epoxidation reaction and the collected oil phase fraction is subjected to the refining treatment with the aqueous alkali solution.

12. The refining treatment method of a liquid reaction mixture obtained from an epoxidation reaction of 1,5,9-cyclododecatriene as claimed in claim 3, wherein the oil phase fraction is collected from the liquid reaction mixture obtained from the epoxidation reaction and the collected oil phase fraction is subjected to the refining treatment with the aqueous alkali solution.

13. The refining treatment method of a liquid reaction mixture obtained from an epoxidation reaction of 1,5,9-cyclododecatriene as claimed in claim 4, wherein the oil phase fraction is collected from the liquid reaction mixture obtained from the epoxidation reaction and the collected oil phase fraction is subjected to the refining treatment with the aqueous alkali solution.

14. The refining treatment method of a liquid reaction mixture obtained from an epoxidation reaction of 1,5,9-cyclododecatriene as claimed in claim 2, wherein, after the refining treatment of the liquid reaction mixture obtained from the epoxidation reaction with the aqueous alkali solution is completed, the oil phase fraction is collected from the refining-treated liquid reaction mixture.

15. The refining treatment method of a liquid reaction mixture obtained from an epoxidation reaction of 1,5,9-cyclododecatriene as claimed in claim 3, wherein, after the refining treatment of the liquid reaction mixture obtained from the epoxidation reaction with the aqueous alkali solution is completed, the oil phase fraction is collected from the refining-treated liquid reaction mixture.

16. The refining treatment method of a liquid reaction mixture obtained from an epoxidation reaction of 1,5,9-cyclododecatriene as claimed in claim 4, wherein, after the refining treatment of the liquid reaction mixture obtained from the epoxidation reaction with the aqueous alkali solution is completed, the oil phase fraction is collected from the refining-treated liquid reaction mixture.

17. A method of isolating 1,2-epoxy-5,9-cyclododecadiene comprising distilling the oil phase fraction collected and then refining-treated, or refining-treated and then collected, in accordance with the method as claimed in claim 6.

18. A method of isolating 1,2-epoxy-5,9-cyclododecadiene comprising distilling the oil phase fraction collected and then refining-treated, or refining-treated and then collected, in accordance with the method as claimed in claim 11.

19. A method of isolating 1,2-epoxy-5,9-cyclododecadiene comprising distilling the oil phase fraction collected and then refining-treated, or refining-treated and then collected, in accordance with the method as claimed in claim 14.

* * * * *